(12) United States Patent
Murray et al.

(10) Patent No.: US 12,128,126 B2
(45) Date of Patent: *Oct. 29, 2024

(54) HAIR TREATMENT COMPOSITION

(71) Applicant: Conopco, Inc., Englewood Cliffs, NJ (US)

(72) Inventors: Andrew Malcolm Murray, Neston (GB); Anne-Sophie Piggott, West Kirby (GB)

(73) Assignee: Conopco, Inc., Englewood Cliffs, NJ (US)

( * ) Notice: Subject to any disclaimer, the term of this patent is extended or adjusted under 35 U.S.C. 154(b) by 663 days.

This patent is subject to a terminal disclaimer.

(21) Appl. No.: 17/284,874

(22) PCT Filed: Oct. 8, 2019

(86) PCT No.: PCT/EP2019/077190
§ 371 (c)(1),
(2) Date: Apr. 13, 2021

(87) PCT Pub. No.: WO2020/088894
PCT Pub. Date: May 7, 2020

(65) Prior Publication Data
US 2021/0386657 A1      Dec. 16, 2021

(30) Foreign Application Priority Data

Oct. 31, 2018 (EP) .................... 18203729

(51) Int. Cl.
| | |
|---|---|
| A61K 8/896 | (2006.01) |
| A61K 8/891 | (2006.01) |
| A61K 8/898 | (2006.01) |
| A61Q 5/12 | (2006.01) |

(52) U.S. Cl.
CPC .............. *A61K 8/896* (2013.01); *A61K 8/891* (2013.01); *A61Q 5/12* (2013.01)

(58) Field of Classification Search
None
See application file for complete search history.

(56) References Cited

U.S. PATENT DOCUMENTS

| | | |
|---|---|---|
| 2001/0051142 A1 | 12/2001 | Duden et al. |
| 2005/0180943 A1 | 8/2005 | Uehara |
| 2014/0230262 A1 | 8/2014 | Lounsbury |
| 2016/0158128 A1 | 6/2016 | Marsh et al. |
| 2016/0310404 A1 | 10/2016 | Schrott et al. |
| 2018/0280270 A1 | 10/2018 | Rughani et al. |
| 2022/0031600 A1 | 2/2022 | Murray et al. |

FOREIGN PATENT DOCUMENTS

| | | |
|---|---|---|
| CN | 1325682 | 12/2001 |
| CN | 1917854 | 2/2007 |
| EP | 2014016350 | 1/2014 |
| JP | 2007522226 | 8/2007 |
| JP | 2010030943 | 2/2010 |
| JP | 2012171890 | 9/2012 |
| JP | 2015517539 | 6/2015 |
| JP | 2016537381 | 12/2016 |
| WO | WO9949836 | 10/1999 |
| WO | WO2005079737 A | 9/2005 |
| WO | WO2010003793 | 1/2010 |
| WO | WO2012152722 | 11/2012 |
| WO | WO2013045382 | 4/2013 |
| WO | WO2013174575 | 11/2013 |
| WO | WO2015075062 | 5/2015 |
| WO | WO2015110506 | 7/2015 |
| WO | WO2015110510 | 7/2015 |
| WO | WO2015110511 | 7/2015 |
| WO | WO2016172407 | 10/2016 |
| WO | WO2017042048 | 3/2017 |
| WO | WO2017106401 | 6/2017 |
| WO | WO2020088893 | 5/2020 |

OTHER PUBLICATIONS

Search Report and Written Opinion in EP18203680; Jan. 21, 2019; European Patent Office (EPO).
Search Report and Written Opinion in PCTEP2019077178; Dec. 17, 2019; .; World Intellectual Property Org. (WIPO).
Search Report and Written Opinion in PCTEP2019077190; Dec. 17, 2019; .; World Intellectual Property Org. (WIPO).
Innovations in hair care; Dksh; Jul. 4, 2017; pp. 1-36.
IPRP2 in PCTEP2019077178; Sep. 23, 2020; World Intellectual Property Org. (WIPO).
Search Report and Written Opinion in EP18203729; Jan. 31, 2019; European Patent Office (EPO).

*Primary Examiner* — Kyung S Chang
(74) *Attorney, Agent, or Firm* — Byrne Poh LLP; Nina R. Horan

(57) ABSTRACT

The present invention is in the field of rinse-off conditioner compositions; in particular, relates to rinse-off conditioner compositions with improved conditioning benefits. Silicones are a commonly used conditioning agent and thus improved deposition of silicones is always desired. It is therefore an object of the present invention to provide improved silicone deposition and also improved sensory of hair. It has been found that the above objects can be achieved by a conditioner composition comprising a specific combination of silicones.

12 Claims, No Drawings

HAIR TREATMENT COMPOSITION

CROSS REFERENCE TO RELATED APPLICATION

This application is a U.S. National Stage Application under 35 U.S.C. § 371 of International Application No. PCT/EP2019/077190, filed on Oct. 8, 2019, which claims the benefit of European Application No. 18203729.1, filed on Oct. 31, 2018, the entire disclosures of which are hereby incorporated by reference for any and all purposes.

FIELD OF THE INVENTION

The present invention is in the field of rinse-off conditioner compositions; in particular, relates to rinse-off conditioner compositions with improved conditioning benefits.

BACKGROUND OF THE INVENTION

Frizz is generally known as hair that does not align with the surrounding hairs, but stands up or curls independently, creating a fuzzy or irregular texture. Generally, hair gets frizzy on days when there is humid weather and the level of moisture in the air is high. As a result, hair appears dry and frizzy instead of smooth, shiny and defined. The appearance of frizz and loss of shine and smoothness are associated with a perception of poor hair health.

A common method of providing conditioning benefits to the hair is through the use of conditioning agents such as cationic surfactants and polymers, high melting point fatty compounds, low melting point oils, silicone compounds, and mixtures thereof. Silicones are commonly used conditioning agents and thus improved deposition of silicones is always desired.

It is therefore an object of the present invention to provide improved silicone deposition.

It is another object of the present invention to provide a composition with improved conditioning benefits.

It is yet another object of the present invention to provide improved sensory of hair.

Surprisingly, it has been found that the above objects can be achieved by a conditioner composition comprising a specific combination of silicones.

SUMMARY OF THE INVENTION

Accordingly, in a first aspect, the present invention provides a rinse-off conditioner composition for hair comprising 0.1 to 10% by weight of a conditioning surfactant; and a silicone combination of 0.1 to 0.3% by weight of an amino functional silicone and 0.5 to 6% by weight of a silicone blend of dimethicone and amodimethicone in a ratio of 9:1.

In a second aspect, the invention provides use of the composition according to claims 1 to 4 for improved silicone deposition onto hair.

In a third aspect, the invention provides a method of treatment of hair for improved silicone deposition comprising the steps in sequence of applying to the hair the composition according to the invention; allowing the composition to remain on hair for 0 to 10 minutes; and rinsing off with water.

In the context of the present invention, the reference to "hair" typically means mammalian hair including scalp hair, facial hair and body hair, more preferably hair on the human head and scalp.

These and other aspects, features and advantages will become apparent to those of ordinary skill in the art from a reading of the following detailed description and the appended claims. For the avoidance of doubt, any feature of one aspect of the present invention may be utilised in any other aspect of the invention. The word "comprising" is intended to mean "including" but not necessarily "consisting of" or "composed of." In other words, the listed steps or options need not be exhaustive. It is noted that the examples given in the description below are intended to clarify the invention and are not intended to limit the invention to those examples per se. Similarly, all percentages are weight/weight percentages unless otherwise indicated. Except in the operating and comparative examples, or where otherwise explicitly indicated, all numbers in this description indicating amounts of material or conditions of reaction, physical properties of materials and/or use are to be understood as modified by the word "about".

Numerical ranges expressed in the format "from x to y" are understood to include x and y. When for a specific feature multiple preferred ranges are described in the format "from x to y", it is understood that all ranges combining the different endpoints are also contemplated.

DETAILED DESCRIPTION OF THE INVENTION

In a first aspect, the present invention relates to a rinse-off conditioner composition comprising a conditioning surfactant and a silicone combination.

Conditioning Surfactant

The composition according to the invention comprises one or more conditioning surfactants which are cosmetically acceptable and suitable for topical application to the hair.

Suitable conditioning surfactants are selected from cationic surfactants, used singly or in admixture. Examples include quaternary ammonium cationic surfactants corresponding to the following general formula:

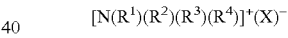

in which $R^1$, $R^2$, $R^3$, and $R^4$ are each independently selected from (a) an aliphatic group of from 1 to 22 carbon atoms, or (b) an aromatic, alkoxy, polyoxyalkylene, alkylamido, hydroxyalkyl, aryl or alkylaryl group having up to 22 carbon atoms; and X is a salt-forming anion such as those selected from halide, (e.g. chloride, bromide), acetate, citrate, lactate, glycolate, phosphate nitrate, sulphate, and alkylsulphate radicals.

The aliphatic groups can contain, in addition to carbon and hydrogen atoms, ether linkages, and other groups such as amino groups. The longer chain aliphatic groups, e.g., those of about 12 carbons, or higher, can be saturated or unsaturated.

Specific examples of such quaternary ammonium cationic surfactants of the above general formula are cetyltrimethylammonium chloride, behenyltrimethylammonium chloride (BTAC), cetylpyridinium chloride, tetramethylammonium chloride, tetraethylammonium chloride, octyltrimethylammonium chloride, dodecyltrimethylammonium chloride, hexadecyltrimethylammonium chloride, octyldimethylbenzylammonium chloride, decyldimethylbenzylammonium chloride, stearyldimethylbenzylammonium chloride, didodecyldimethylammonium chloride, dioctadecyldimethylammonium chloride, tallowtrimethylammonium chloride, cocotrimethylammonium chloride, dipalmitoylethyldimethylammonium chloride, PEG-2 oleylammonium chloride and salts of these, where the chloride is replaced by other halide (e.g., bromide), acetate, citrate, lactate, glycolate, phosphate nitrate, sulphate, or alkylsulphate.

In a preferred class of cationic surfactant of the above general formula, $R^1$ is a $C_{16}$ to $C_{22}$ saturated or unsaturated, preferably saturated, alkyl chain and $R^2$, $R^3$ and $R^4$ are each independently selected from $CH_3$ and $CH_2CH_2OH$, preferably $CH_3$.

Specific examples of such preferred quaternary ammonium cationic surfactants are cetyltrimethylammonium chloride (CTAC), behenyltrimethylammonium chloride (BTAC) and mixtures thereof.

Alternatively, primary, secondary or tertiary fatty amines may be used in combination with an acid to provide a cationic surfactant suitable for use in the invention. The acid protonates the amine and forms an amine salt in situ in the hair care composition. The amine is therefore effectively a non-permanent quaternary ammonium or pseudo-quaternary ammonium cationic surfactant.

Suitable fatty amines of this type include amidoamines of the following general formula:

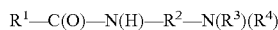

$R^1$—C(O)—N(H)—$R^2$—N($R^3$)($R^4$)

in which $R^1$ is a fatty acid chain containing from 12 to 22 carbon atoms, $R^2$ is an alkylene group containing from one to four carbon atoms, and $R^3$ and $R^4$ are each independently, an alkyl group having from one to four carbon atoms.

Specific examples of suitable materials of the above general formula are stearamidopropyldimethylamine, stearamidopropyldiethylamine, stearamidoethyldiethylamine, stearamidoethyldimethylamine, palmitamidopropyldimethylamine, palmitamidopropyldiethylamine, palmitamidoethyldiethylamine, palmitamidoethyldimethylamine, behenamidopropyldimethylamine, behenamidopropyldiethylamine, behenamidoethyldiethylamine, behenamidoethyldimethylamine, arachidamidopropyldimethylamine, arachidamidopropyldiethylamine, arachidamidoethyldiethylamine, arachidamidoethyldimethylamine, and diethylaminoethylstearamide.

Also useful are dimethylstearamine, dimethylsoyamine, soyamine, myristylamine, tridecylamine, ethylstearylamine, N-tallowpropane diamine, ethoxylated (with 5 moles of ethylene oxide) stearylamine, dihydroxyethylstearylamine, and arachidyl behenylamine.

Particularly preferred is stearamidopropyldimethylamine.

The acid used may be any organic or mineral acid which is capable of protonating the amine in the hair care composition. Suitable acids include hydrochloric acid, acetic acid, tartaric acid, fumaric acid, lactic acid, malic acid, succinic acid, and mixtures thereof. Preferably, the acid is selected from the group consisting of acetic acid, tartaric acid, hydrochloric acid, fumaric acid, lactic acid and mixtures thereof.

Mixtures of any of the above-described cationic surfactants may also be suitable.

The conditioning surfactant is present in the composition in a concentration of 0.1 to 10%, preferably at least 0.5%, more preferably at least 1%, still more preferably at least 2%, even more preferably at least 3% or even at least 4% but typically not more than 9%, preferably not more than 8%, more preferably not more than 7%, still more preferably not more than 6%, even more preferably not more than 5% by weight of the composition.

Silicone Combination

The present invention comprises a silicone combination of an amino functionalised silicone and a silicone blend.

Amino Functionalised Silicones

By "amino functionalised silicone" is meant a silicone containing at least one primary, secondary or tertiary amine group, or a quaternary ammonium group. Examples of suitable amino functionalised silicones include: polysiloxanes having the CTFA designation "amodimethicone".

The amino functionalised silicones of the present invention include emulsified particles of an amino functionalised silicone of general formula:

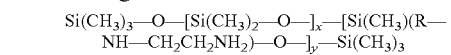

$Si(CH_3)_3$—O—$[Si(CH_3)_2$—O—$]_x$—$[Si(CH_3)(R$—NH—$CH_2CH_2NH_2)$—O—$]_y$—$Si(CH_3)_3$

Wherein x+y is a number from about 50 to about 500, and wherein R is an alkylene group having from 2 to 5 carbon atoms.

Preferably, the number x+y is in the range of from about 100 to about 300.

The amino functionalised silicone is insoluble in the aqueous matrix and so is present in an emulsified form, with the silicone present as dispersed particles.

The amino functionalised silicones suitable for use in the invention need to have a mole % amino functionality of at least 1 mole %. Range from 1 to 8 mole %.

Particle size is less than 10 microns.

Specific examples of amino functionalised silicones suitable for use in the invention are the aminosilicone oils DC2-8220, DC2-8166 (all ex Dow Corning).

Pre-formed emulsions of amino functional silicone are also available from suppliers of silicone oils such as Dow Corning and General Electric. Specific examples include DC939 Cationic Emulsion and the non-ionic emulsions DC2-7224, DC2-8467, DC2-8177 and DC2-8154 (all ex Dow Corning).

The amino functionalised silicone is present in the composition in a concentration of 0.1 to 0.3%, preferably 0.1 to 0.2% by weight of the composition.

Silicone Blend

The silicone blend used in the present invention is a blend of dimethicone and amodimethicone in a ratio of 9:1.

Dimethicone used in the present invention preferably has a viscosity of at least 500,000 $mm^2$/sec at 25° C. and a molecular weight of at least 200,000 Daltons.

By "dimethicone" is meant polydimethylsiloxane.

Amodimethicone, also known as amino functionalised silicone used in the present invention preferably has a viscosity of less than 500,000 $mm^2$/sec at 25° C. and a molecular weight of less than 200,000 Daltons.

Preferably, the amodimethicone has a mole percent amino functionality in the range of 0.3 to 8, preferably 0.5 to 4.

The silicone blend is present in the composition in a concentration of 0.5 to 6%, preferably at least 1%, more preferably at least 1.5%, still more preferably at least 2%, even more preferably at least 3% but typically not more than 5%, preferably not more than 4%, more preferably not more than 3.5% by weight of the composition.

Ratio of the Amino Functional Silicone to the Silicone Blend

The amino functional silicone and the silicone blend is present in the composition in a ratio of 1:1.5 to 1:60, preferably 1:5 to 1:55, more preferably 1:10 to 1:50, still more preferably 1:15 to 1:45, even more preferably 1:20 to 1:40 or 1:25 to 1:35.

Fatty Material

Hair conditioner compositions of the invention preferably additionally comprise fatty materials. The combined use of fatty materials and cationic surfactants in conditioning compositions is believed to be especially advantageous, because this leads to the formation of a structured lamellar or liquid crystal phase, in which the cationic surfactant is dispersed.

By "fatty material" is meant a fatty alcohol, an alkoxylated fatty alcohol, a fatty acid or a mixture thereof.

Preferably, the alkyl chain of the fatty material is fully saturated.

Representative fatty materials comprise from 8 to 22 carbon atoms, more preferably 16 to 22. Examples of suitable fatty alcohols include cetyl alcohol, stearyl alcohol and mixtures thereof. The use of these materials is also advantageous in that they contribute to the overall conditioning properties of compositions of the invention.

Alkoxylated, (e.g. ethoxylated or propoxylated) fatty alcohols having from about 12 to about 18 carbon atoms in the alkyl chain can be used in place of, or in addition to, the fatty alcohols themselves. Suitable examples include ethylene glycol cetyl ether, polyoxyethylene (2) stearyl ether, polyoxyethylene (4) cetyl ether, and mixtures thereof.

The level of fatty material in conditioners of the invention is suitably from 0.01 to 15, preferably from 0.1 to 10, and more preferably from 0.1 to 5 percent by weight of the total composition. The weight ratio of cationic surfactant to fatty alcohol is suitably from 10:1 to 1:10, preferably from 4:1 to 1:8, optimally from 1:1 to 1:7, for example 1:3.

When present, the fatty material is present in the composition in a concentration of 0.1 to 15%, preferably at least 2%, more preferably at least 4%, still more preferably at least 6%, even more preferably at least 8% but typically not more than 14%, preferably not more than 13%, more preferably not more than 11%, even more preferably not more than 10%, still more preferably not more than 9% by weight of the composition.

Optional Ingredients

Compositions of this invention may contain any other ingredient normally used in hair treatment formulations, including further silicone or non-silicone hair conditioning oils. These other ingredients may include viscosity modifiers, preservatives, colouring agents, polyols such as glycerine and polypropylene glycol, chelating agents such as EDTA, antioxidants, fragrances, antimicrobials and sunscreens. Each of these ingredients will be present in an amount effective to accomplish its purpose. Generally, these optional ingredients are included individually at a level of up to 5% by weight of the total composition.

In a second aspect, the present invention relates to use of the composition according to the invention for improved silicone deposition onto hair.

In a third aspect, the present invention relates to a method of treatment of hair for improved silicone deposition comprising the steps in sequence of applying to the hair the composition according the invention; allowing the composition to remain on hair for 0 to 10 minutes; and rinsing off with water.

The invention will now be further described by reference to the following Examples. In the Examples, all percentages are by weight based on total weight, unless otherwise specified.

EXAMPLES

Example 1: Effect of the Silicone Combination on Silicone Deposition

Hair conditioning compositions were prepared, having ingredients as shown in table 1 below. Example 1 represents composition according to the invention and Comp A is a comparative example with compositions outside the scope of the claim.

TABLE 1

| Ingredients | Tradename | Wt % in composition Comp A | Wt % in composition Example 1 |
|---|---|---|---|
| Fatty alcohol | Ginol 1618 TA | 4 | 4 |
| Surfactant | Genamin BTLF (70% active) | 2.85 | 2.85 |
| Chelating agent | Disodium EDTA (100% active) | 0.05 | 0.05 |
| Preservatives | Glydant 2000 (55% active) | 0.46 | 0.46 |
| Fragrance | SNOW QUEEN CDT 5 (100% active) | 0.5 | 0.5 |
| Silicone blend of dimethicone and amodimethicone in a ratio of 9:1 | Xiameter MEM-7134 (70% active) | 4.28 | — |
| Silicone combination | 4.28% silicone blend (70% active) of dimethicone and amodimethicone in a ratio of 9:1 + 1% amino functional silicone DC2 8177(14% active) | — | 5.28 |
| Water | Water | Upto 100 | Upto 100 |

TA Measurement Protocol (Dry Friction)

5 of 2.5 g×6" WIDE Flat metal switches were used per treatment. All the switches were washed and treated prior to testing using the switch washing protocols outlined below. The black tubes used for the measurements were supplied pre-cut and was washed before use with a mild detergent (14% SLES). The tubes were also dried prior to use. The pre-cut and washed black tubes were mounted onto the metal probes. The switches were then mounted onto the kit, and a weight that replicates the consumer interaction with hair was placed on top of the switch. The frictional force was output as g·mm.

Silicone Deposition Protocol: XRF Analyzer 5 of 2.5 g×6" hair switches were washed according to the switch washing protocol below. Once the switches were dried, they were mounted on 40 mm XRF cells. A negative control set of switches (to give a baseline reading for the hair) was included with each experiment. The mounted cells were then measured for silicone deposition, using XRF analyzer. The calibration used was Si_TA 40 mm.

Switch Washing Protocol

The switches were wetted under the tap. Cleansing shampoo was applied to the switch. The switch was massaged for 30 seconds and then rinsed under the tap for 30 seconds. This was repeated. The wet switches were then detangled using a comb. This was repeated for all 5 switches. The switches were then dried overnight at 20° C./50% RH.

This was followed by the treatment with the compositions in table 1.

Result

Table 2 shows the data on silicone deposition and dry friction at different stages of wash.

TABLE 2

| | Sets | | | | | |
|---|---|---|---|---|---|---|
| | 1 treatment | | 1x washout | | 4x washout | |
| | Silicone deposition (ppm) | Dry friction | Silicone deposition (ppm) | Dry friction | Silicone deposition (ppm) | Dry friction |
| Comp A | 1152 | 22083 | 421 | 30043 | 120 | 39676 |
| Ex 1 | 4426 | 17341 | 3061 | 19087 | 1510 | 20598 |

The results show that the composition according to the invention (Ex 1) delivers superior silicone deposition and lesser dry friction even after multiple washes. Dry friction is an indicator of consumer sensory such as smoothness, softness and ease in combing. Lesser the dry friction, better is the sensory.

The invention claimed is:

1. A rinse-off conditioner composition for hair comprising
    a 0.1 to 10% by weight of a conditioning surfactant; and
    b a silicone combination comprising:
        i 0.1 to 0.3% by weight of an amino functional silicone; and
        ii 2 to 4% by weight of a silicone blend of dimethicone and amodimethicone in a ratio of 9:1; and
    c 0.1 to 15% by weight of a fatty material;
    wherein a weight ratio of the amino functional silicone to the silicone blend of dimethicone and amodimethicone ranges from about 1:6.7 to 1:40; and
    wherein a weight ratio of the conditioning surfactant to the fatty material ranges from 10:1 to 1:10.

2. The conditioner composition according to claim 1 wherein the composition comprises 0.1% by weight of amino functional silicone.

3. The conditioner composition according to claim 1 for improved silicone deposition onto hair.

4. A method of treatment of hair for improved silicone deposition comprising:
    a applying to the hair the composition according to claim 1;
    b allowing the composition to remain on hair for 0 to 10 minutes; and
    c rinsing off with water.

5. The conditioner composition according to claim 1, wherein the conditioning surfactant comprises cetyltrimethylammonium chloride (CTAC), behenyltrimethylammonium chloride (BTAC) or mixtures thereof.

6. The conditioner composition according to claim 1, wherein the composition comprises 1 to 6% by weight of a conditioning surfactant.

7. The conditioner composition according to claim 1, wherein the amino functional silicone comprises aminosilicone oil.

8. The conditioner composition according to claim 1, wherein the ratio of the amino functional silicone to the silicone blend of dimethicone and amodimethicone ranges from about 1:20 to 1:40.

9. The conditioner composition according to claim 1, wherein the composition comprise 0.1 to 10% of the fatty material.

10. The conditioner composition according to claim 9, wherein the composition comprise 2 to 9% of the fatty material.

11. The conditioner composition according to claim 9, wherein the fatty material comprises a fatty alcohol, an alkoxylated fatty alcohol, a fatty acid or a mixture thereof.

12. The conditioner composition according to claim 11, wherein the fatty alcohol comprises cetyl alcohol, stearyl alcohol or mixtures thereof.

* * * * *